United States Patent
Stamler et al.

(10) Patent No.: US 7,776,925 B2
(45) Date of Patent: Aug. 17, 2010

(54) REVERSING, POSTPONING OR PREVENTING THE OCCURRENCE OF GTN TOLERANCE AND/OR GENERATION OF REACTIVE OXYGEN SPECIES FROM MITOCHONDRIA

(75) Inventors: Jonathan S. Stamler, Chapel Hill, NC (US); Zhiqiang Chen, Durham, NC (US); Thomas Munzel, Hamburg (DE)

(73) Assignee: Duke University, Durham, NC (US)

( * ) Notice: Subject to any disclaimer, the term of this patent is extended or adjusted under 35 U.S.C. 154(b) by 1126 days.

(21) Appl. No.: 10/980,801

(22) Filed: Nov. 4, 2004

(65) Prior Publication Data

US 2005/0148612 A1    Jul. 7, 2005

Related U.S. Application Data

(63) Continuation-in-part of application No. 10/508,957, filed as application No. PCT/US03/03126 on Feb. 24, 2003, now Pat. No. 7,691,907.

(60) Provisional application No. 60/519,289, filed on Nov. 13, 2003, provisional application No. 60/361,689, filed on Mar. 6, 2002, provisional application No. 60/372,415, filed on Apr. 16, 2002, provisional application No. 60/377,204, filed on May 3, 2002.

(51) Int. Cl.
*A61K 31/095* (2006.01)
*A61K 31/045* (2006.01)

(52) U.S. Cl. .................. 514/706; 514/738

(58) Field of Classification Search ............ 514/706, 514/738
See application file for complete search history.

(56) References Cited

U.S. PATENT DOCUMENTS

| 4,910,313 | A | * | 3/1990 | Welter et al. ............ 546/265 |
| 5,480,888 | A | * | 1/1996 | Kodama et al. .......... 514/310 |
| 5,489,610 | A | | 2/1996 | Fung et al. ............. 514/506 |
| 5,645,839 | A | * | 7/1997 | Chobanian et al. ...... 424/400 |
| 2001/0056068 | A1 | * | 12/2001 | Chwalisz et al. ........ 514/21 |
| 2003/0086916 | A1 | * | 5/2003 | Goligorsky et al. ...... 424/94.4 |

FOREIGN PATENT DOCUMENTS

WO    WO 03/075832    9/2003

OTHER PUBLICATIONS

Hink, Ulrich, et al., "Role for peroxynitrite in the inhibition of prostacyclin synthase in nitrate tolerance", J. Am. Col. Cardiol., vol. 42, No. 10, p. 1835-1837 Nov. 19, 2003. (Abstract only).
Sydow, K., et al, The Journal of Clinical Investigation 113(3), 482-489 (Feb. 2004).
Science Daily, Duke University Popular Drug for Chest Pain May Promote Blood Vessel Damage (Nitroglycerin) posted on Web Feb. 07, 2004.

* cited by examiner

*Primary Examiner*—Zohreh A Fay
(74) *Attorney, Agent, or Firm*—Bacon & Thomas, PLLC

(57) ABSTRACT

A patient in need of nitroglycerin therapy is treated with nitroglycerin and agent that prevents inhibition of or reverses inhibition of mtALDH and/or the generation of reactive oxygen species from mitochondria, e.g., a mitochondrial antioxidant which is not a reducing agent or a dithiol, e.g., ebselen or uric acid. Nitroglycerin dosage can be regulated and inhibiting agent dosage can be regulated and tolerance postponed by monitoring blood level of active mtALDH and dosing in response to determined level of active mtALDH.

1 Claim, No Drawings

REVERSING, POSTPONING OR PREVENTING THE OCCURRENCE OF GTN TOLERANCE AND/OR GENERATION OF REACTIVE OXYGEN SPECIES FROM MITOCHONDRIA

CROSS-REFERENCE TO RELATED APPLICATIONS

This application is a continuation-in-part of U.S. application Ser. No. 10/508,957 filed Oct. 5, 2004 which is a 371 of PCT/US03/03126 filed 24 Feb. 2003 which claims priority from 60/361,689 (6 Mar. 2000), 60/372,415 (16 Apr. 2002) and 60/377,204 (3 May 2002). This application also claims the benefit of U.S. Provisional Application No. 60/519,289, filed 13 Nov. 2003, the whole of which is incorporated herein by reference.

TECHNICAL FIELD

This invention is directed to therapies for which nitroglycerin (GTN) administration is indicated.

BACKGROUND OF THE INVENTION

WO 03/075832A2 indicates that attenuated biotransformation of GTN by the enzyme mitochondrial aldehyde dehydrogenase (mtALDH, ALDH2) underlies nitrate tolerance, i.e., the loss of clinical sensitivity to GTN. WO 03/075832A2 discloses a number of therapies for reversing, postponing or preventing the occurrence of nitrate tolerance.

SUMMARY OF THE INVENTION

It has been discovered herein that nitrate tolerance can be reversed, postponed or prevented by administering agents to a patient starting on or on nitroglycerin therapy, a therapeutically effective amount of an agent which prevents inhibition of or reverses inhibition of mtALDH and/or prevents or reverses the generation of reactive oxygen species from the mitochondria (which can attenuate GTN action by oxidizing and thereby inactivating mtALDH). This discovery is not anticipated when GTN is administered to a patient on general antioxidant therapy because general antioxidant therapy does not significantly postpone the occurrence of nitrate tolerance because it is not directed at mitochondria where oxidation occurs that inactivates mtALDH.

It has also been discovered herein that nitroglycerin dosage can be regulated and dosage of agent that inhibits or reverses inhibition of mtALDH can be regulated, so as to postpone or prevent the occurrence of nitroglycerin tolerance, in response to monitoring blood level of mtALDH.

In one embodiment of the invention herein, denoted the first embodiment, the invention is directed to a method of treating a patient in need of nitroglycerin therapy comprising administering to the patient a therapeutically effective amount of nitroglycerin and a nitrate tolerance reversing, postponing or preventing amount of agent that prevents inhibition of or reverses inhibition of mtALDH. In one case, said agent is a mitochondrial antioxidant which is not a dithiol or a reducing agent.

In another embodiment of the invention herein, denoted the second embodiment, the invention is directed to a method for treating a patient in need of nitroglycerin therapy comprising administering to that patient a therapeutically effective amount of nitroglycerin and a nitrate tolerance reversing, postponing or preventing amount of agent that prevents or reverses the generation of reactive oxygen species from the mitochondria. In one case, said agent is a mitochondrial antioxidant which is not a dithiol or a reducing agent. In another case which overlaps the first case, said agent is a peroxynitrite scavenger which is effective to reverse, postpone or prevent the occurrence of nitrate tolerance.

In another embodiment of the invention herein, denoted the third embodiment, the invention is directed to a method for treating a patient in need of nitroglycerin therapy and for regulating nitroglycerin dosage in the treatment of a patient in need of nitroglycerin therapy which comprises monitoring blood level of the patient of active mtALDH and administering nitroglycerin to the patient in an effective amount for amelioration of the disorder for which nitroglycerin therapy is being employed that does not inactivate mtALDH or postpones inactivation of mtALDH compared to conventional dosage, in response to determined level of mtALDH.

mtALDH referred to in the disclosure of the invention herein is human mtALDH and is a known enzyme and is described in Vasilion, V., Chemico-Biological Interactions 129, 1-19 (2000), unless otherwise stated. However any mitochondrial mtALDH could fulfill criteria for determining inhibitor of mtALDH.

The term "reactive oxygen species" is used herein to mean superoxide and its reduced oxygen derivatives and/or peroxynitrite (product of nitric oxide and superoxide interaction).

DETAILED DESCRIPTION

Objectives of the invention are to maintain or enhance the activity of mtALDH by preventing or postponing or reducing oxidation of the enzyme and to maintain mitochondrial function during the course of GTN therapy, thereby preserving response to GTN.

The disorders of the patients in need of nitroglycerin therapy for the first, second and third embodiments of the invention herein, include unstable coronary syndromes including myocardial infarction, restenosis, heart failure, hypertension, obstructive, inflammatory or interstitial lung disease, rectal spasm and stroke.

In the first, second and embodiments of the invention herein, the nitroglycerin is administered in a dose used for the disorders treated, by the routes of administration normally used, or preferably at 30 to 60% of said dosages (e.g., a dose of 1 mcg/min to 1,000 mcg/min IV). For angina the dosage is a pain ameliorating amount, a blood pressure reducing amount or an amount that prevents or decreases infarct size. For restenosis, the dosage is a heart vessel relaxing amount, or an amount that attenuates restenosis or its consequences. For heart failure, the amount is a blood flow increase causing amount or a blood pressure reducing amount. For an obstructive, inflammatory or interstitial lung disease, e.g., asthma, the amount is an airway relaxing amount or an oxygenation increasing amount. For rectal spasm, the amount is a spasm ameliorating amount. For portal hypertension, it is a portal pressure lowering amount. For stroke, the amount is a neuroprotecting amount.

We turn now to the nitrate tolerance reversing, postponing or preventing agents herein.

Testing for agent that prevents inhibition or reverses inhibition of mtALDH is carried out by using the test mixture described in Background Example 4 of WO 03/075832A2 together with test compound and determining whether mtALDH oxidation is prevented.

Determination of agent that prevents or reverses the generation of reactive oxygen species is carried out by testing as described in respect to determining activity for ebselen and uric acid at pages 484 and 486 of Sydow, K., et al, The Journal of Clinical Investigation 1133(3), 482-489 (February 2004) in paragraphs headed "Measurement of ROS production from isolated heart mitochondria" and "Mitochondrial ROS production".

The agents for the first, second and third embodiments herein include dithiols and reducing agents capable of activating mtALDH as set forth as page 12 of WO 03/075832A2, as well as, the agents listed in Claim 8 of U.S. 2003/0086916A1. As indicated above, in one case, the agents are mitochondrial antioxidants which are not dithiols or reducing agents. These include, or example, 2-phenyl-1,2-benzisoselenazol-3(2H)-one which is known as ebselen, uric acid, mitoquinone, coenzyme$Q_{10}$, glutathione, phenyl-butyl-nitrone, manganese-superoxide dismutase, peptides SS-02 and SS-31 and Vitamin E. Preferred agents are uric acid and 2-phenyl-1,2-benzisoselenazol-3(2H)-one which is known as ebselen.

The nitrate tolerance reversing, postponing or preventing amounts of agents depend on the agent administered and can range, for example, from 0.01 µmol/kg to 2 mmol/kg. For uric acid and ebselen, the dosage can range, for example, from 1 to 50 mg/kg or 5 to 40 µM concentration in blood for uric acid and 50 to 150 µM concentration in blood for ebselen. In respect to postponing the occurrence of nitrate tolerance, the amount should be such as to postpone the occurrence of tolerance for at least one day as determined by preservation of mtALDH activity.

The routes of administration include oral, transdermal, intravenous, inhaled and intramuscular. For uric acid and ebselen the route of administration is preferably oral or intravenous.

For the third embodiment, blood level of mtALDH can be monitored, e.g., by isolating the enzyme from a blood sample as described at page 32 of WO 03/075,832A2 and measuring activity of mtALDH in the presence of NTG by the method of Background Example 4 of WO 03/075832A2. The monitoring is also useful when GTN therapy is used in combination with a administration of agents pursuant to the first and second embodiments herein. The method of the third embodiment allows administration of a dose of GTN that does not inactivate mtALDH, or is slower to inactivate mtALDH than a conventional dose, e.g., a low dose of GTN, e.g., 60-90% of conventional dose by regulating dosage in response to level of active mtALDH determined in the monitoring. When agent that prevents or reverses inhibition of mtALDH is also administered, the dosage of the agent is readily regulated in response to the level of active mtALDH determined in the monitoring of blood level of mtALDH.

The efficacy of the invention is supported by the following background examples. The invention is illustrated by the following working examples.

BACKGROUND EXAMPLE 1

Animals deficient in mtALDH do not respond to GTN.

BACKGROUND EXAMPLE 2

Dogs given agent to inhibit mtALDH have impaired coronary vasodilator response and no response to GTN.

BACKGROUND EXAMPLE 3

Mitochondrial stock solutions were diluted to final total protein concentrations of approximately 0.1 mg/ml in 0.5 ml of MOPS buffer. The dye L-012 (100 µM) was used as described in Nishinaka, Y. et al, Biochem. Biophys. Res. Commun. 193, 554-559 (1993) and Sohn, H. Y. et al, J. Vasc. Res. 36, 456-464 (1999) to quantify ROS following addition of succinate (4 mM final concentration). Chemiluminescence was monitored over 5 minutes using a Lumar LB9507 from Berthold Technologies (Wildbad, Germany), and the signal at 5 minutes was expressed as counts per minute. ROS production was quantified in mitochondria from GTN-treated animals (in vivo) and in mitochondria exposed to increasing concentrations of GTN in vitro. In selected experiments, mitochondria were pre-incubated with DTT (100 µM) or the antioxidants uric acid (20 µM) and ebselen (Eb; 100 µM).

Formation of ROS in heart mitochondria from rats treated with NTG for 3 days was increased approximately 50% compared with controls. Furthermore, incubation of isolated mitochondria from control animals with GTN (5 and 50 µM) caused a dose-dependent increase in ROS production. Uric acid (20 µM) almost completely inhibited the L-012-enhanced chemiluminescence derived from GTN (50 µm). DTT and ebselen (each 100 µM) also entirely prevented the increase in ROS generated by in vitro incubation with 5 mM GTN.

EXAMPLE I

A 70-year old patient with persistent angina is treated by infusion of nitroglycerin. Administration of ebselen at 10 mg/kg thrice/day prevents the occurrence of nitrate tolerance and prevents increase in level of reactive oxygen species and preserves activity of mtALDH.

EXAMPLE II

A 67-year old patient with unstable angina becomes tolerant to infusion of nitroglycerin and develops angina. Administration of uric acid, I.V., to obtain a blood concentration of 20 µM causes reverse of tolerance and restoration of mtALDH activity and resolution of angina.

VARIATIONS

The forgoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. A method for treating a patient in need of nitroglycerin therapy which comprises monitoring blood level of active mtALDH and administering nitroglycerin to the patient in an effective amount for amelioration of the disorder for which nitroglycerin therapy is being employed that does not inactivate mtALDH or postpones inactivation of mtALDH compared to conventional dosage, in response to determined level of active mtALDH.

* * * * *